(12) United States Patent
Korhonen (10) Patent No.: US 7,052,174 B2
(45) Date of Patent: May 30, 2006

(54) DEVICE FOR DETERMINING CHANGES IN DIMENSION DUE TO TEMPERATURE FLUCTUATION

(75) Inventor: Charles J. Korhonen, Etna, NH (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 72 days.

(21) Appl. No.: 10/941,958

(22) Filed: Sep. 16, 2004

(65) Prior Publication Data

US 2006/0056483 A1    Mar. 16, 2006

(51) Int. Cl.
*G01N 25/16*    (2006.01)

(52) U.S. Cl. ............... 374/55; 374/5; 374/7; 374/57; 374/142; 73/766; 73/803

(58) Field of Classification Search ............... 374/7, 374/55–57, 45, 142, 5; 73/766–803, 865.6
See application file for complete search history.

(56) References Cited

U.S. PATENT DOCUMENTS

| | | | | |
|---|---|---|---|---|
| 2,692,747 | A | * | 10/1954 | Strauss ................... 108/51.3 |
| 4,092,869 | A | * | 6/1978 | Kimball ..................... 73/665 |
| 4,429,575 | A | | 2/1984 | Akishika |
| 4,729,246 | A | * | 3/1988 | Melgaard et al. .......... 73/865.6 |
| 4,787,752 | A | * | 11/1988 | Fraser et al. ................. 374/45 |
| 5,118,945 | A | * | 6/1992 | Winschuh et al. ......... 250/341.4 |
| 5,143,450 | A | * | 9/1992 | Smith et al. .................. 374/12 |
| 5,147,136 | A | * | 9/1992 | Hartley et al. ................ 374/57 |
| 5,248,200 | A | * | 9/1993 | Walsh ......................... 374/45 |
| 5,610,344 | A | * | 3/1997 | Ueda et al. ................ 73/865.6 |
| 5,613,776 | A | * | 3/1997 | Turner et al. ................. 374/57 |
| 5,704,582 | A | * | 1/1998 | Golembiewski et al. .... 248/500 |
| 6,029,526 | A | | 2/2000 | Feldman et al. |
| 6,591,691 | B1 | * | 7/2003 | Kim et al. ..................... 73/803 |
| 6,941,818 | B1 | * | 9/2005 | Rakowski ..................... 73/762 |
| 6,971,262 | B1 | * | 12/2005 | Marchal et al. ............. 73/54.01 |

\* cited by examiner

*Primary Examiner*—Diego Gutierrez
*Assistant Examiner*—Megann E. Vaughn
(74) *Attorney, Agent, or Firm*—Earl H. Baugher, Jr.

(57) ABSTRACT

An apparatus for non-destructively testing the response of a specimen to temperature change. An embodiment temperature cycles a specimen, such as a wet mortar beam, dynamically measuring change in dimension and the temperature of the specimen during the cycle. Among other elements, the apparatus employs an accelerometer, a thermistor, a thermocouple, a temperature controller, linear variable differential transducers (LVDTs), an FFT device, a data logger and a heat tape controller. A typical cycle involves using liquid nitrogen to reduce the temperature in an insulated test chamber from ambient to less than −60° C. and returning to ambient by dispersing the nitrogen with a source of ambient air. Further, in select embodiments, the apparatus measures fundamental frequencies induced by a micro-hammer as measured transversely along a dimension of a specimen during the cooling-warming cycle. Also provided is a method for testing specimens using devices representative of embodiments of the present invention.

32 Claims, 4 Drawing Sheets

DEVICE FOR DETERMINING CHANGES IN DIMENSION DUE TO TEMPERATURE FLUCTUATION

STATEMENT OF GOVERNMENT INTEREST

Under paragraph 1(a) of Executive Order 10096, the conditions under which this invention was made entitle the Government of the United States, as represented by the Secretary of the Army, to the entire right, title and interest therein of any patent granted thereon by the United States. This patent and related ones are available for licensing. Contact Sharon Borland at 703 428-9112 or Phillip Stewart at 601 634-4113.

BACKGROUND

A serious problem associated with installing concrete in cold climates is deterioration caused by freezing and thawing, commonly referred to as frost damage. Several theories have been developed to explain frost damage but it is recognized that such damage only happens to moist concrete. Damage occurs when water inside concrete freezes, causing swelling and micro-cracking. Repeated cycles of freezing and thawing cause the initial cracks to grow and coalesce into larger cracks that eventually manifest themselves on the surface.

The current method of testing the resistance of concrete to frost damage is to subject concrete specimens to repeated cycles of freezing and thawing inside a cabinet specially designed for that purpose. Typically, the test specimens are cycled between 40° F. and 0° F. and back again in not less than two or more than five hours. The testing continues until the specimens have been subjected to 300 cycles or until they have failed (ASTM C 666). This is both time consuming and expensive.

When a concrete specimen is cooled much below 0° C., certain transformations occur. The specimen shrinks initially, but at temperatures below 0° C., it expands suddenly. Further cooling causes it to shrink again until cooled to a very low temperature where it expands once more. In general, as a specimen cools it will gradually stiffen causing it to vibrate at successively higher frequencies. At the onset of freezing when a specimen expands suddenly, it vibrates at a higher frequency than before it expanded. This may be due to ice forming in the pores, the concrete stiffening and manifesting this as a higher fundamental frequency of vibration.

Concrete, when frozen, is considered to be frost susceptible if it dilates and to be resistant to frost action if it does not dilate. Thus, a device that measures the change in length of concrete specimens as they are cooled would enable the relative freeze-thaw durability of concrete to be determined. This may be possible within as little as a single freeze-thaw cycle. If dilation occurs, the deterioration process has begun and the concrete will fail with additional freezing and thawing cycles. Further, initial dilation may not be visible as cracks, although the larger the initial dilation, the more frost susceptible is the concrete. However, it is possible that a specimen that dilates during a single freeze-thaw cycle can return to its original length. If this happens, one may conclude that no frost damage has occurred and that the specimen is durable. Thus, a device designed to monitor length changes throughout a freeze-thaw cycle would be beneficial in determining the susceptibility of various forms of concrete to frost damage. Further, a device that measures the fundamental frequency of vibration of the "excited" specimen subjected to a cooling regimen as above provides another non-destructive means for detecting and correlating these cooling-warming cycles.

DETAILED DESCRIPTION

An apparatus is provided for dynamically determining changes in dimension of a specimen caused by temperature variation. An embodiment of the present invention comprises means for simultaneously subjecting at least three like a specimens to at least one cycle of cooling and warming; means for sensing and reporting temperature to enable control thereof, means for detecting and reporting change in at least one dimension of a first like specimen during the cycling; means for detecting and reporting the instantaneous temperature of a second like specimen during the cycling, means for impacting at least a third like specimen in order to cause vibration therein; and means for detecting and reporting at least the frequency of the vibration.

In select embodiments of the present invention, the means for subjecting comprises one or more base plates; at least an innermost and one outer enclosures; means for support disposed on the base plates, so as to hold the enclosures on the base plate; means for retaining specimens, the means for retaining disposed within at least one of the enclosures; means for insulating at least one of the enclosures; coolant; air; at least one programmable proportional temperature controller to control the amount of air and coolant provided to the air gap around the innermost enclosure; one or more thermistors, in operable communication with the controller and at least one of the specimens, held in the innermost enclosure; one or more needle valves in operable communication with the temperature controller; and one or more insulated lines in operable communication with the needle valves, the insulated line providing coolant from an external source, such as a liquid nitrogen bottle.

The means for support may comprise blocks at the corners of an outermost of the enclosures. The means for retaining may comprise one or more biased rods disposed at each of two opposing ends of the first like specimen, one or more rollers disposed beneath each of the first and second like specimens and a fixed support disposed beneath the third like specimen. The means for retaining may further comprise one or more tubes in which the biased rods are enclosed, the tube in operable communication with at least one of the enclosures.

The means for insulating may comprise one or more outer enclosures disposed to maintain one or more air gaps between at least an innermost of the enclosures and an outer one of the enclosures and insulation material disposed adjacent at least one inner surface of an outer one of the enclosures so as to form an air gap between the insulation and the innermost enclosure. Coolant such as liquid nitrogen may be used to control the temperature of the innermost enclosure.

In select embodiments of the present invention, the means for detecting and reporting change in dimension comprises one or more linear variable differential transducers (LVDTs) in contact with each biased rod. In select embodiments of the present invention, one or more data loggers are used to take the data from the LVDTs.

In select embodiments of the present invention, the biased rods are kept at or near ambient temperature by the use of one or more heat tape power supplies and heat tape wound around the tubes enclosing the biased rods.

In select embodiments of the present invention, means for measuring one or more fundamental frequencies of vibration of the third like specimens are provided. These means for measuring comprise: one or more micro-hammers disposed to contact the third like specimens at pre-specified times, one or more FFT devices to take data from the specimen and pass it to a data logger, and one or more accelerometers to provide data from the third like specimen to an FFT device.

In select embodiments of the present invention, the means for measuring temperature comprise: one or more thermocouples attached to the second like specimens, the output of the thermocouples fed to a data logger.

Also provided in an embodiment of the present invention is a method for measuring changes in dimension of a first specimen due to temperature fluctuation, the first specimen like each of a second and third specimen, comprising:

providing an apparatus comprising:
 a first detector mechanism for detecting and reporting change data correlated to change in length of the first like specimen; a second detector mechanism for detecting and reporting data correlated to the instantaneous temperature of the second like specimen; a third detector mechanism for detecting data correlated to instantaneous frequency of vibration of the third like specimen; a first control sensor for providing data to control temperature, the first control sensor in operable communication with the first like specimen; a first support mechanism for containing the first like specimen, the first support mechanism incorporating one or more biased rods in operable communication with the first like specimen; a second support mechanism for containing the second like specimen; a third support mechanism for containing the third like specimen; an innermost enclosure for enclosing the like specimens and at least part of the support mechanisms; one or more outer enclosures for enclosing the innermost enclosure, the outer enclosure providing at least some insulation material between the outer enclosure and the innermost enclosure disposed so as to form an air gap between the insulation and the innermost enclosure; one or more controllers in operable communication with one or more first control sensors; an impact mechanism in operable communication with at least a controller, the impact mechanism suitably positioned for providing impacts to the third like specimen; one or more mechanisms for varying temperature within the innermost enclosure, the temperature varying mechanism in operable communication with at least one or more controllers, the first control sensor and the innermost enclosure; support blocks in operable communication with an outer enclosure; and one or more base support plates in operable communication with at least the support blocks, one or more controllers and the mechanism for varying temperature; one or more data loggers in operable communication with at least the detector mechanisms and a controller; and one or more FFT devices in operable communication with the third detector mechanism and a data logger;

inserting first, second and third like specimens in the apparatus, the first like specimen being the test specimen, the second like specimen provided for taking temperature measurements and the third like specimen provided for taking frequency measurements;

instrumenting each first like specimens with one or more first detector mechanisms and one or more of the first control sensors;

instrumenting each of the second like specimens with one or more second detector mechanisms;

instrumenting each of the third like specimens with one or more third detector mechanisms;

varying the temperature of all the like specimens over a pre-specified range for a pre-specified time; and impacting the third like specimens via an impact mechanism at pre-specified times; and at pre-specified intervals, providing data from one or more of the detection mechanisms and data from the FFT device to one or more data loggers. The pre-specified intervals may be determined by passage of time, change in temperature, and combinations thereof.

In select embodiments of the present invention, the method involves instrumenting a first specimen with a first control sensor comprising at least one thermistor for facilitating temperature control and a first detector mechanism comprising at least one linear variable differential transducer in operable communication one or more of the biased rods, instrumenting a second specimen with said second detector mechanism comprising at least one thermocouple, and instrumenting a third specimen with a third detector mechanism comprising at least one accelerometer for outputting data correlated with instantaneous frequency to an FFT device.

In select embodiments of the present invention, the method involves stimulating the third specimen via one or more micro-hammers striking the third specimen at pre-specified intervals to establish a fundamental frequency of response in the third specimen.

In select embodiments of the present invention, the method involves varying the temperature through at least one freeze-thaw cycle. In select embodiments of the present invention, the temperature is varied from ambient temperature to approximately −60° C. and returned to ambient temperature over a pre-specified period via introducing a coolant to lower temperature and ambient air to raise temperature.

In select embodiments of the present invention, the method provides the specimens as mortar beams. In select embodiments of the present invention, the method provides the mortar beams as wet mortar beams.

An embodiment of the present invention provides an apparatus for non-destructively testing the response of a specimen to temperature change, such as a mortar beam susceptible to frost damage. An embodiment of the present invention comprises means for subjecting the specimen to at least one cycle of freezing and thawing, means for measuring a change in dimension of the specimen during the cycle, and means for measuring the temperature of the specimen during the cycle. Further, in select embodiments of the present invention, the apparatus measures fundamental frequencies induced by a micro-hammer as measured transversely along a dimension of the specimen during the cooling-warming cycle.

An embodiment of the present invention also provides a method of non-destructively testing the response of a specimen to temperature change, such as testing the resistance of a mortar beam to frost damage. An embodiment of the method comprises: subjecting three like specimens to at least one cycle of freezing and thawing, measuring a change in dimension of a first one of the specimens during the cycle; measuring the temperature of a second one of the specimens during the cycle; impacting one or more times a third one of the specimens to establish one or more resonant signals; and determining the frequency of the one or more resonant signals resultant from the impacts.

Figure 1:
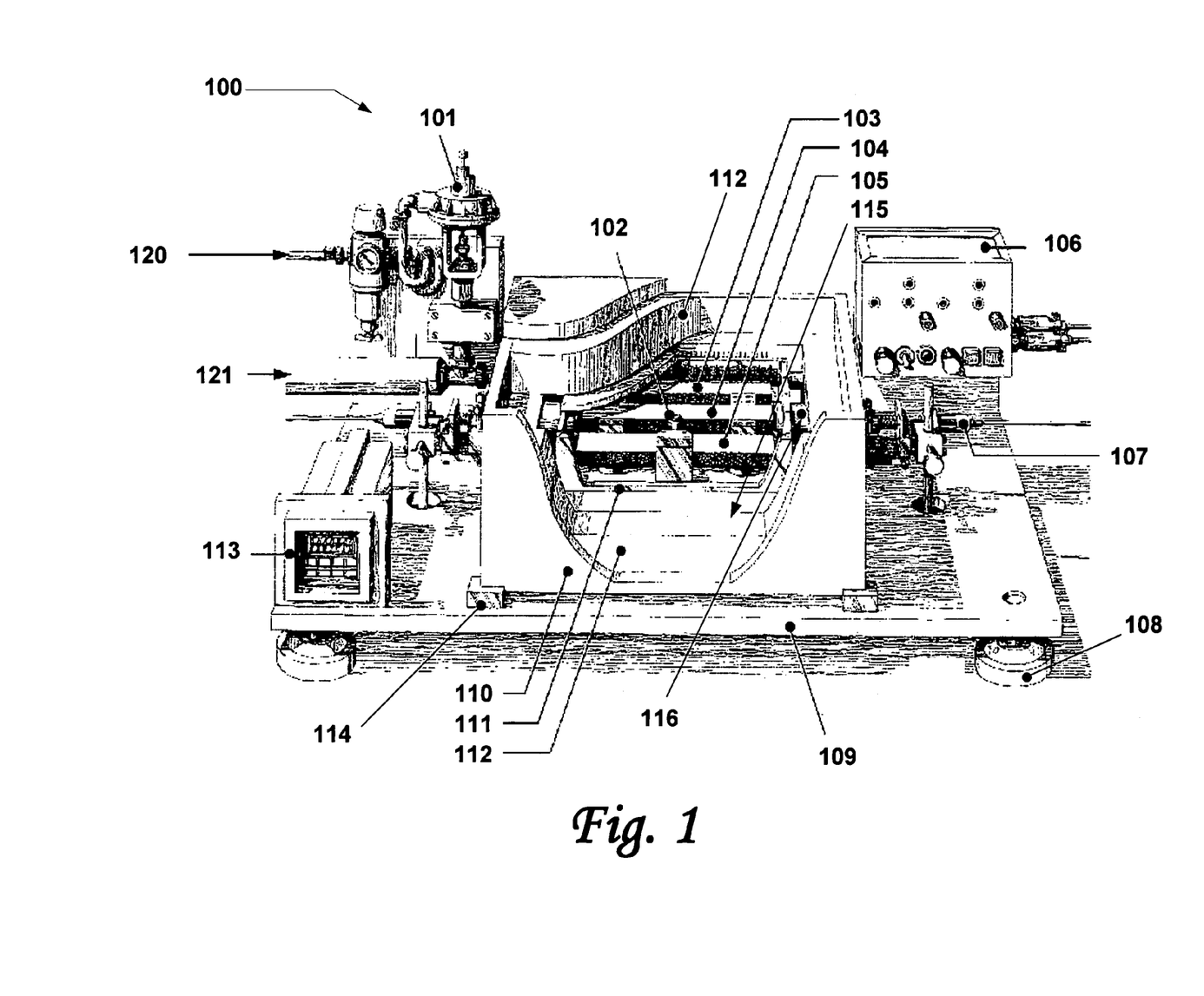
FIG. 1 is a cutaway drawing of an apparatus embodying the invention.

Refer to FIG. 1. In select embodiments of the present invention, the apparatus 100 includes a test chamber in the form of an external box 110 (in FIG. 1 shown as a cutaway to reveal internal components). The external box 110 may be constructed of any suitably robust material, such as plywood. The external box 110 is supported on a base plate 109 by blocks 114 placed at its four corners. The base plate 109 and the blocks 114 are made from any suitably robust material, such as aluminum. For purposes such as leveling or providing space under the base plate 109 for easily grasping the apparatus 100 for moving, adjustable feet 108 are threaded into the base plate 109. The inside walls, floor, and top cover of the external box 110 are lined with suitable insulation 112, such as extruded polystyrene. Inboard of the insulation 112 is an air gap 115 around an internal box 111 (in FIG. 1 shown as a cutaway to reveal internal components), made from any suitably robust material, such as aluminum, for housing a test specimen, such as a beam 104 constructed from mortar. The air gap 115 separates the internal box 111 from the insulation 112.

The internal box 111 is cooled by nitrogen gas provided from liquid nitrogen (LN) 121 that flows in the air gap 115 between the inner box 111 and the insulation 112 that lines the inside of the outer box 110. A programmable proportional temperature controller 113, such as an OMEGA™, Model 2001 temperature controller, regulates the internal chamber temperature by sensing a thermistor 504 (location shown in FIG. 5) placed beneath the beam 104 at its approximate center. The nitrogen 121 flows from ports in a finned evaporator (not shown separately) behind the box 111. Flow is controlled by a needle valve 101 in an insulated line (not shown separately) connected to a liquid nitrogen tank (not shown separately) and to the finned evaporator. Air 120 is used to control the flow of liquid nitrogen through the needle valve 101. The temperature controller 113 regulates the opening on the needle valve 101 to set a pre-specified cooling rate.

Length change measurements are made with linear variable differential transducers 107, such as TRANS-TEK Series 350 transducers, that monitor the movement of rods 501 (shown in FIG. 5) contacting either end of the beam 104 under test and that protrude out from the external box 110. The rods 501, which run inside a metal tube 116 shown in FIG. 1, are lightly spring loaded, such as shown in FIG. 5 with coil springs 502, to follow the beam 104 as it contracts and expands. The tube 116 is wrapped with heat tape 402 (not shown in FIG. 1, but indicated functionally in FIG. 4) powered by a heat tape power supply 106 to assure that the rods 501 remain near ambient temperature. Thus, the measurements recorded by the transducers 107 do not have to be adjusted for thermal movement of the rods 501. As added assurance, the rods 501 may be fabricated from an alloy of low thermal expansion, such as the nickel-iron alloy INVAR™. The two transducers 107 are connected to a data logger 407(not shown in FIG. 1, but indicated functionally in FIG. 4), such as an OMNIDATA™ Model 824 data logger. They may be set to read every minute.

Three beams 103, 104, 105, e.g., concrete beams made from the same mortar mixture, may be placed inside the box 111 for each test. The beams 103, 104, 105 are supported at approximately the quarter points of their length. The first beam 104 is the beam under test. It is placed on rollers 503 (as shown in FIG. 5) in the middle of the internal box 111. The rollers 503 are constructed of a suitably robust material such as nylon.

Figure 4:
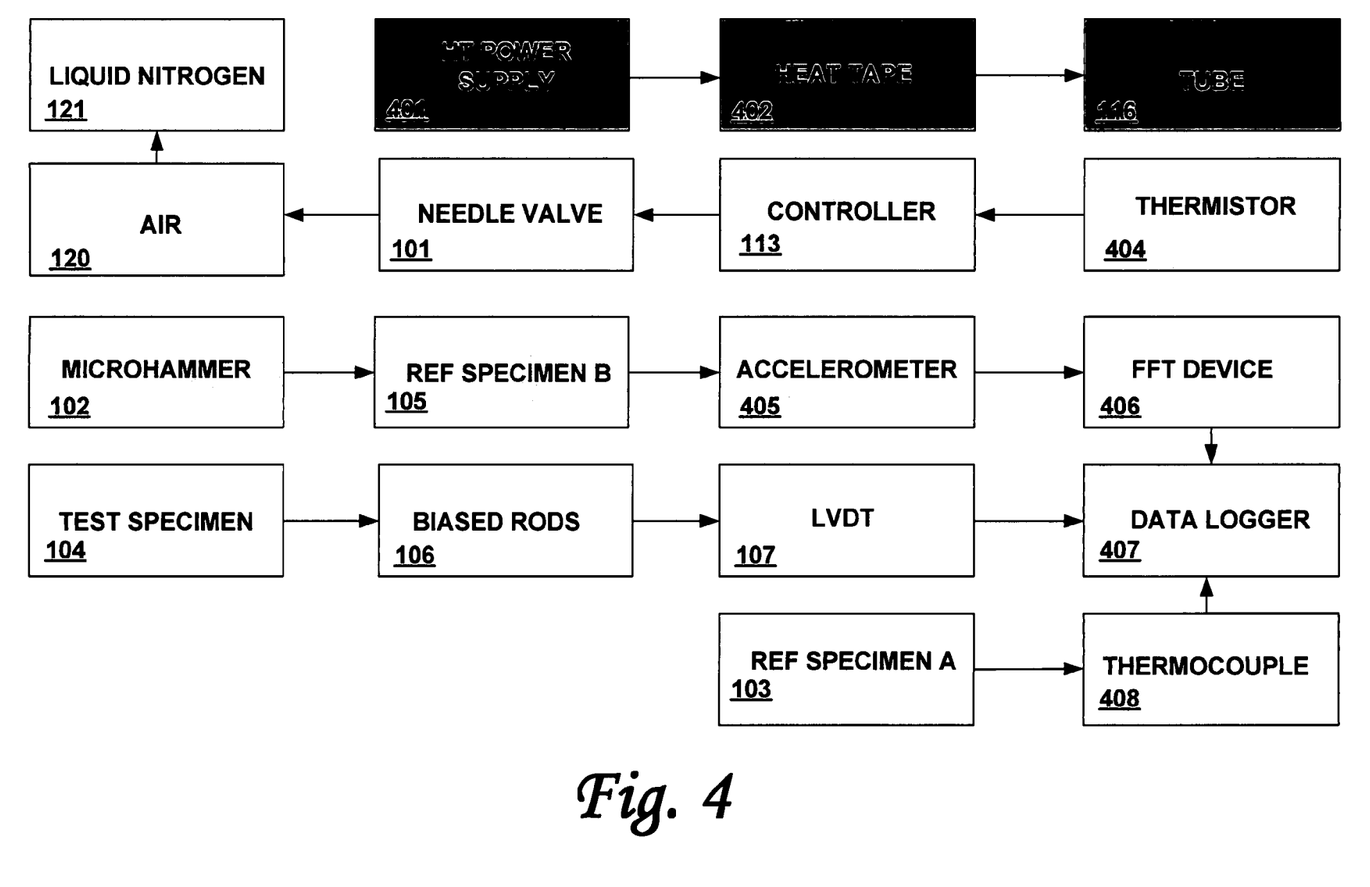
FIG. 4 is a block diagram showing the relationship among various components of an embodiment of the present invention.
Figure 5:
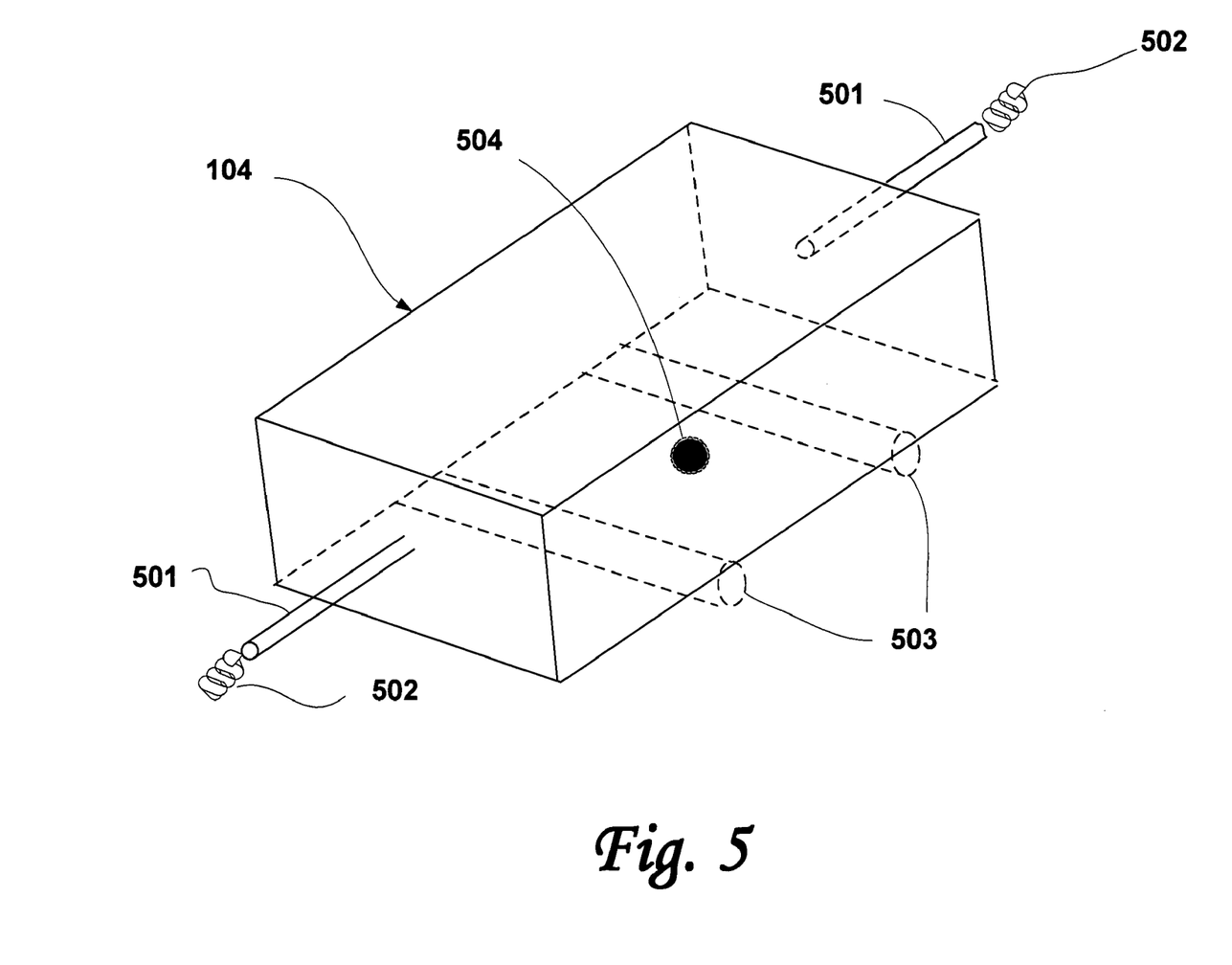
FIG. 5 is an isometric view of a test specimen showing the relationship of some components of an embodiment of the present invention to the test specimen as installed in the embodiment.

The second beam 103, reference specimen A in FIG. 4, is instrumented with a thermocouple 408 (not shown in FIG. 1, but indicated functionally in FIG. 4) at its center of mass. The second beam 103 is also placed on rollers 503 similar to that of the first beam 104 but at the back of the internal box 111. The rollers 503 are constructed of a suitably robust material such as nylon. The second beam 103 is instrumented to quantify the temperature of the other beams 104, 105 used during testing.

A third beam 105, reference specimen B in FIG. 4, is placed on supports (not shown separately) at the front of the internal box 111. The supports are constructed of a suitably robust resilient material such as rubber. A solenoid-actuated micro-hammer 102 is disposed above the third beam 105. An accelerometer 405 (not shown in FIG. 1, but indicated functionally in FIG. 4) is attached to one end of the third beam 105. The output from the accelerometer 405 is converted into a frequency response by a Fast Fourier Transform (FFT) device 406 (not shown in FIG. 1, but indicated functionally in FIG. 4), such as a model SA-77 RION™ Signal Analyzer. The third beam 105 is used to measure the fundamental vibration frequency that would be experienced by the like first beam 104.

In operation, the contraction and expansion of the first beam 104 is recorded by continuously monitoring a dimension of the beam 104, such as the length of the beam 104, as it is cooled from ambient temperature to below −60° C. and returned to ambient temperature. In addition, the fundamental vibration frequency of the beam 104 may be estimated during the cycle using a solenoid-actuated micro-hammer 102 to strike the like third beam 105 at pre-specified times.

Refer to FIG. 4. The relationship among major components of an embodiment of the present invention is displayed. Liquid nitrogen 121 is dispersed by a needle valve 101 in turn controlled by a controller 113 that uses the input from a thermistor 404 to maintain a pre-specified temperature profile.

The rods 501 (FIG. 5) are maintained at a near-ambient temperature by heat provided by a heat tape power supply 401 to heat tape 402 wrapped about the immovable tube 116 in which the rods 502 are contained.

The micro-hammer 102 strikes the beam 105 (Ref. specimen B) to which an accelerometer 405 has been affixed at one end. The output of the accelerometer 405 is fed to an FFT device 406 and outputted to a data logger 407.

The test specimen (first beam) 104 is placed on rollers 503 between two biased rods 106 to each of which a linear variable differential transformer (LVDT) 107 is attached. The output of the LVDTs 107 is fed to a data logger 407.

The reference specimen A (second beam) 103 is fitted with a thermocouple 408 for taking temperature data as an estimate of the temperature of the test specimen (first beam) 104. The output of the thermocouple is fed to the data logger 407.

Figure 2:
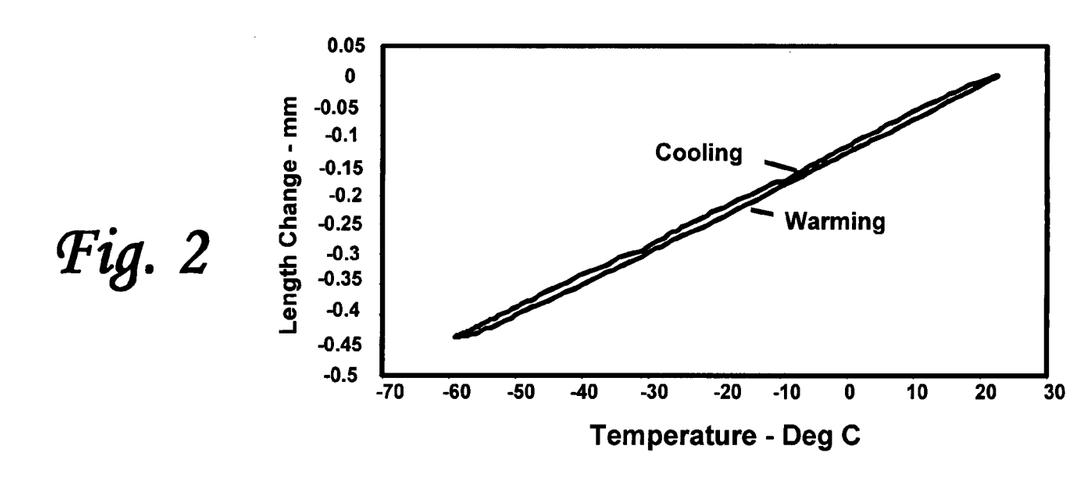
FIG. 2 depicts the length change versus temperature of a cooling-warming cycle for an aluminum alloy beam.

The ability of an embodiment of the present invention to accurately measure change in dimension was demonstrated with an aluminum alloy (6061-T6) of the same dimensions as a mortar beam 104 to be tested. Refer to FIG. 2 showing length-change curves for a cooling-heating cycle of an aluminum alloy beam (not shown separately). The two curves are linear with the exception of minor perturbations caused by the cooling system cycling. This demonstrates that the aluminum beam contracted and expanded linearly, the slope of the curves representing a measure of the thermal coefficient of the alloy. Although the cooling and warming curves did not exactly trace each other, this is inconsequential since measurements were obtained while the beam was changing temperature. Because the beam was not in thermal equilibrium, length change lagged temperature change. A manifestation of this lag is that the measured slope, $21.1 \times 10^{-6}$ m/° C., does not quite match the value published for the alloy's established thermal coefficient of expansion, $23.0 \times 10^{-6}$ m/° C. Lyman, T. (Ed.), *Metals Handbook., Volume 1, Properties and Selection of Metals,* American Society for Metals, Metals Park, Ohio, 1961. For purposes of demonstration, the length-change line plotted nearly linear and the length change measurements returned to zero. The aluminum beam was tested three times and all three times it produced the same results.

EXAMPLE

Length changes were measured for wet and dry mortar beam specimens of approximate dimensions 12.7×25.4×254 mm (0.5 in×1.0 in.×10 in.). Also measured was the change in response frequency of wet mortar as a function of temperature. Providing a relatively thin specimen (12.7 mm) assured temperature uniformity throughout the cross-section of the sample. Several calibrations prior to testing indicated the largest difference between the center and surface temperatures of 10° C. This test recorded the contraction and expansion of the mortar beams as they froze and thawed. This was accomplished by continually monitoring the length of a beam 104 as it cooled from ambient temperature, i.e., 20° C., to below −60° C.

Figure 3:
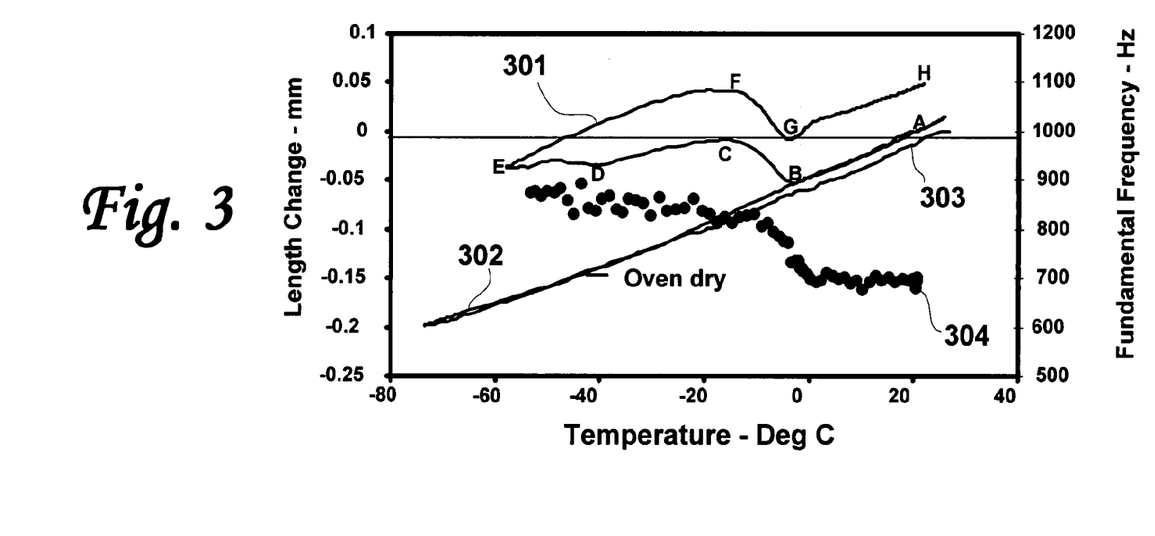
FIG. 3 depicts the length change versus temperature for a cooling-warming cycle of both wet and dry mortar beams and the frequency response versus temperature of a cooling-warming cycle of the wet mortar beam.

Refer to FIG. 3. The length change curve 301 for a "wet" mortar beam exhibited a pronounced hysteresis between cooling and warming and consisted of seven distinct regions, their endpoints identified by labels A through H. In region AB, on cooling between 20 and −5° C., the wet mortar initially contracted linearly in the range of $9–15 \times 10^{-6}$ m/° C., depending on the mortar. This compares favorably to published values for the thermal coefficient of expansion of mortar, $7–12 \times 10^{-6}$ m/° C. A length-change curve 302 for an oven-dried mortar beam is also shown. The "dry" beam contracts linearly (as in curve 302) at an average rate of $9 \times 10^{-6}$ m/° C. down to −70° C. and closely retraces (as in curve 303) the contraction curve 302 back to ambient (20° C.) temperature. Comparing the two curves 301, 302 and the published values for coefficient of expansion, length changes in region AB for the "control" curves are determined to be thermally induced.

In region BC, between approximately −5 and −20° C., the wet mortar beam 104 expanded significantly. Some of this expansion may be caused by conversion of water to ice inside large capillary pores. The temperature at which ice first forms is considered the freezing point of the mortar. The expansion between −5 and −20° C. is caused by water migrating from smaller pores to the bulk ice as well as the water freezing in the large capillaries. This accreting of ice in limited spaces causes expansive stress.

In region CD, most of the large capillary pores froze and water from the small pores continued to migrate to the locations of the bulk ice. This is equivalent to drying and is manifested as shrinkage. Thus, there were three processes occurring between approximately −20 and −40° C.: thermal contraction of the matrix, shrinkage (contracting) due to drying within the small pores, and ice build up in the coarse pores (large capillaries). The net effect is contraction, though at a lower rate than at initiation.

In region DE, at approximately −40° C., the wet mortar beam 104 expanded for a second time. This may be caused by water in the smaller pores freezing in place and generating hydraulic stress rather than migrating to the bulk ice.

On initiation of warming, as indicated by region EF, the wet mortar beam 104 again expanded, exhibiting significant expansion from approximately 60 to −20° C. One might expect the beam to contract as ice in the smallest pores begins to melt and reduce in volume. However, the expansion of the mortar matrix in this region mimics that of region AB, i.e., the measured thermal coefficient is the same. A possible explanation for this expansion could be that both the un-melted ice in the coarse pores and the "cement paste" were thermally expanding, as they should as they warm, to counteract the decrease in volume of ice in the small pores. The net effect was the thermal expansion of the mortar matrix itself. It is also possible that the water that diffused from the small "gel pores" migrated back during thawing. It is not clear what mechanism was causing the mortar beam 104 to lengthen in this region, but it is clear that an embodiment of the present invention enables researchers to determine this in an efficient manner.

Melting of the ice in the larger pores causes the wet mortar to contract in the region FG. In this region, all of the small pores melted and reabsorbed water. The tensional force in the water in the small pores was reduced. Thus, the volume change of ice to water is the direct cause of the contraction measured between −20 and 0° C.

At 0° C. all ice had melted and normal thermal expansion predominated from 0 to 20° C. It is significant to note that the wet mortar beam 104 did not return to its original length when warmed to ambient (20° C.) temperature, exhibiting residual expansion that indicates permanent frost damage.

Thus, it can be stated that when concrete is cooled to temperatures below 0° C., certain transformations occur. As noted above, the mortar beam specimen 104 shrunk initially, but at a certain temperature below 0° C., it suddenly expanded. Further cooling caused it to shrink again until it cooled to a very low temperature, whereupon it expanded once more. FIG. 3 also shows a frequency response curve 304 of the change in frequency of the wet mortar beam 104 as a function of temperature. As expected, the wet mortar gradually stiffened as it cooled from 20 to 0° C. and somewhat beyond. At the region BC where it suddenly expanded, the frequency sharply increased as well, as shown in the frequency response curve 304. This demonstrates that anomalies in the freezing process may be detected through frequency measurements and length changes correlated thereto. In this case, the wet mortar beam 104 exhibited a change in frequency response as it expanded while cooling over a certain temperature range. As can be seen from the frequency response curve 304, the frequency continued to increase until the specimen cooled to approximately −20° C., mirroring the expansion in length. Between −20 and 40° C., the specimen gradually increased in frequency, similar to the rate during initial cooling. From −40 to −70° C., the specimen became stiffer, showing a scatter in the frequency response data. It is likely that ice forming within the small pores caused the scatter. Upon warming, the frequency response retraced the frequency response cooling curve 304 fairly well.

Accordingly, all such modifications are intended to be included within the scope of this invention as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

The abstract is provided to comply wit the rules requiring an abstract, which will allow a searcher to quickly ascertain the subject matter of the technical disclosure of any patent issued from this disclosure. 37 CFR § 1.72(b). Any advantages and benefits described may not apply to all embodiments of the invention.

I claim:

1. An apparatus for dynamically quantifying changes in dimension of a specimen caused by temperature variation, comprising:
   means for simultaneously subjecting at least three like specimens to at least one cycle of cooling and warming;
   means for sensing and reporting temperature to enable control thereof, said means for sensing temperature in operable communication with at least a first one of said three like specimens;
   means for detecting and reporting change in at least one dimension of at least said first like specimen during said at least one cycle;
   means for detecting and reporting the instantaneous temperature of at least said second like specimen during said at least one cycle;
   means for impacting at least said third like specimen in order to cause vibration in said third like specimen; and
   means for detecting and reporting at least the frequency of said vibration.

2. The apparatus of claim 1 in which said means for simultaneously subjecting comprises:
   at least one base plate;
   enclosures to include an innermost enclosure and at least one outer enclosure;
   means for support in operable communication with said at least one base plate, said means for support holding said enclosures on said at least one base plate;
   means for retaining said specimens, said means for retaining in operable communication with at least one of said enclosures means for insulating said at least one outer enclosure;
   coolant;
   at least one programmable proportional temperature controller,
   wherein said controller controls the amount of air and said coolant provided to change the temperature of said innermost enclosure;
   at least one thermistor in operable communication with said controller and said first one of said like specimens;
   at least one needle valve in operable communication with at least said temperature controller,
   wherein operation of said needle valve may be facilitated by a source of air; and
   at least one insulated line in operable communication with at least said needle valve,
   wherein said insulated line provides said coolant from an external source.

3. The apparatus of claim 2 in which said means for support comprises at least blocks at the corners of said at least one outer enclosure.

4. The apparatus of claim 2 in which said means for retaining comprises:
   at least one biased rod disposed at each of two opposing ends of said first like specimens;
   at least one roller disposed beneath each of said first and second like specimens; and
   at least one fixed support disposed beneath said third like specimen.

5. The apparatus of claim 4 in which said means for retaining further comprises at least one tube in which said at least one biased rod is enclosed, each said tube in operable communication with at least one of said enclosures.

6. The apparatus of claim 5 in which said means for detecting and reporting change in dimension comprises
   at least one linear variable differential transducer in operable communication with at least one said biased rod.

7. The apparatus of claim 6 further comprising at least one data logger in operable communication with at least each said transducer.

8. The apparatus of claim 7 in which said means for measuring the frequency further comprises means for measuring at least one fundamental frequency of vibration of said third like specimen.

9. The apparatus of claim 8 in which said means for measuring said at least one fundamental frequency comprises:
   at least one micro-hammer disposed to contact said third like specimen at pre-specified times;
   at least one FFT device in operable communication with said data logger; and
   at least one accelerometer in operable communication with said FFT device and said third like specimen.

10. The apparatus of claim 7 in which said means for measuring temperature comprises at least one thermocouple, wherein said thermocouple is in operable communication with said data logger and said second like specimen.

11. The apparatus of claim 6 further comprising:
    at least one heat tape power supply; and
    heat tape,
    wherein said heat tape is wound around said tube to maintain the temperature of each said rod near that of ambient temperature during said at least one cycle.

12. The apparatus of claim 2 in which said means for insulating comprises:
    at least one said outer enclosure disposed to maintain at least one air gap between said innermost enclosure and said at least one outer enclosure; and
    insulation material disposed adjacent both said air gap and at least one inner surface of said at least one outer enclosure.

13. The apparatus of claim 2 in which said coolant is liquid nitrogen.

14. A method for measuring changes in dimension of a first specimen due to temperature fluctuation, said first specimen like each of a second and third specimen, comprising:
    providing an apparatus comprising:
       a first detector mechanism for detecting and reporting change data correlated to change in length of said first like specimen;

a second detector mechanism for detecting and reporting data correlated to the instantaneous temperature of said second like specimen, said second detector mechanism in operable communication with said second like specimen;

a third detector mechanism for generating and detecting data correlated to instantaneous frequency of vibration of said third like specimen, said third detector mechanism in operable communication with said third like specimen;

a first control sensor for providing data to control temperature, said first control sensor in operable communication with said first like specimen;

a first support mechanism for containing said first like specimen, said first support mechanism incorporating at least one biased rod in operable communication with said first like specimen;

a second support mechanism for containing said second like specimen;

a third support mechanism for containing said third like specimen;

an innermost enclosure for enclosing said specimens and at least part of said support mechanisms;

at least one outer enclosure for enclosing said innermost enclosure, said at least one outer enclosure providing at least airspace and at least some insulation material disposed so as to create an air gap between said outer enclosure and said innermost enclosure;

at least one controller in operable communication with at least said first control sensor;

an impact mechanism in operable communication with at least said controller, said impact mechanism suitable for providing impacts to said third like specimen;

at least one mechanism for varying temperature within said innermost enclosure, said temperature varying mechanism in operable communication with at least said controller, at least said first control sensor and at least said air gap;

support blocks in operable communication with at least one said outer enclosure; and at least one base support plate in operable communication with at least said support blocks, said controller and said mechanism for varying temperature;

at least one data logger in operable communication with at least said detector mechanisms and said controller; and at least one FFT device in operable communication with at least said third detector mechanism and said data logger;

inserting first, second and third like specimens in said apparatus, wherein said first like specimen is the test specimen, said second like specimen is provided for taking temperature measurements and said third like specimen is provided for taking frequency measurements;

instrumenting each of said first specimens with at least one said first detector mechanism and at least one said first control sensor; instrumenting each of said second specimens with at least one said second detector mechanism;

instrumenting each of said third specimens with at least one said third detector mechanism;

varying the temperature of all said specimens over a pre-specified range for a pre-specified time;

striking said third specimen via said impact mechanism at pre-specified times; and at pre-specified intervals providing data from at least said detector mechanisms and said FFT device to said data logger.

15. The method of claim 14 in which said first control sensor comprises at least one thermistor, said first detector mechanism comprises at least one linear variable differential transducer in operable communication with at least one said biased rod, said second detector mechanism comprises at least one thermocouple, and said third detector mechanism comprises at least one accelerometer for outputting data correlated to instantaneous frequency to said FFT device.

16. The method of claim 14 striking at least said third like specimen via at least one micro-hammer, said micro-hammer striking said third like specimen at pre-specified times to establish instantaneous fundamental frequencies of response in said third like specimen.

17. The method of claim 14 varying said temperature through at least one freeze-thaw cycle.

18. The method of claim 17 varying said temperature from ambient temperature to approximately −60° C. and returning to ambient temperature over a pre-specified period via introducing a coolant to lower temperature and ambient air to raise temperature.

19. The method of claim 14 providing said specimens as mortar beams.

20. The method of claim 19 providing said mortar beams as wet mortar beams.

21. An instrument that simultaneously subjects at least three like specimens to at least one cycle of cooling and warming to enable quantification of changes in dimension that are caused by temperature variation, said instrument comprising:

at least one base plate;

enclosures to include an innermost enclosure and at least one outer enclosure;

support structure in operable communication with said at least one base plate, said support structure restraining said enclosures on said at least one base plate;

retaining structure for said specimens, said retaining structure in operable communication with at least one of said enclosures;

insulation applied to the inside of said at least one outer enclosure, disposed to form an air gap between said insulation and said innermost enclosure;

coolant;

at least one programmable proportional temperature controller, wherein said controller controls the amount of air and said coolant provided to said innermost enclosure;

at least one thermistor in operable communication with said controller and a first one of said like specimens;

at least one needle valve in operable communication with at least said controller, wherein operation of said needle valve may be facilitated by a source of air; and at least one insulated line in operable communication with at least said needle valve, wherein said insulated line provides said coolant from an external source;

at least one temperature control sensor to enable control of temperature within said innermost enclosure, said sensor in operable communication with at least said first like specimen;

at least one first detection mechanism for detecting and reporting change in at least one dimension of at least said first like specimen;

at least one second detection mechanism for detecting and reporting the temperature of at least said second like specimen;

at least one impact device for striking at least said third like specimen in order to cause vibration in said third like specimen;

at least one third detection mechanism for detecting and reporting at least the frequency of said vibration, and at least one data logging device in operable communication with at least said detection mechanisms.

22. The instrument of claim 21 in which said support structure comprises at least blocks at the corners of said at least one outer enclosure.

23. The instrument of claim 21 in which said retaining structure comprises:

biased rods, at least one each disposed at each of two opposing ends of said first like specimen;

at least one roller disposed beneath each of said first and second like specimens; and at least one fixed support disposed beneath said third like specimen.

24. The instrument of claim 23 in which said retaining structure further comprises at least one tube, each said tube at least partially enclosing at least one said biased rod and in contact with at least one of said enclosures.

25. The instrument of claim 21 in which said coolant is liquid nitrogen.

26. The instrument of claim 24 in which said first detection mechanism comprises at least in part at least one liner variable differential transducer in operable communication with at least one said biased rod.

27. The instrument of claim 24 further comprising:

at least one heat tape power supply; and heat tape, wherein said heat tape is wound round said tube to maintain the temperature of each said rod near that of ambient temperature during each said cycle.

28. The instrument of claim 21 in which said second detection mechanism comprises at least one thermocouple, wherein said thermocouple is in operable communication with at least said data logger and said second like specimen.

29. The instrument of claim 21 in which said third detection mechanism comprises at least one detector for measuring the instantaneous fundamental frequency of vibration of said third like specimen.

30. The instrument of claim 29 in which said mechanism for measuring said fundamental frequency comprises:

at least one micro-hammer disposed to strike said third like specimen at pre-specified times;

at least one FFT device in operable communication with at least said data logger; and at least one accelerometer in operable communication with at least said FFT device and said third like specimen.

31. The instrument of claim 21 in which said specimens are beams composed of mortar.

32. The instrument of claim 31 in which said mortar is wet mortar.

* * * * *